US009289548B2

(12) United States Patent
Kalt et al.

(10) Patent No.: US 9,289,548 B2
(45) Date of Patent: Mar. 22, 2016

(54) ACOUSTIC WARNING LEVEL OPTIMIZATION IN AMBULATORY MEDICAL SYSTEMS

(71) Applicant: Roche Diagnostics International AG, Rotkreuz (CH)

(72) Inventors: Lucas Kalt, Muenchenbuchsee (CH); Axel Remde, Luetzelflueh-Goldbach (CH)

(73) Assignee: Roche Diagnostics International AG, Rotkreuz (CH)

( * ) Notice: Subject to any disclaimer, the term of this patent is extended or adjusted under 35 U.S.C. 154(b) by 274 days.

(21) Appl. No.: 13/773,093

(22) Filed: Feb. 21, 2013

(65) Prior Publication Data

US 2013/0163769 A1    Jun. 27, 2013

Related U.S. Application Data

(63) Continuation of application No. PCT/EP2011/063809, filed on Aug. 11, 2011.

(30) Foreign Application Priority Data

Aug. 23, 2010   (EP) .................................... 10173658

(51) Int. Cl.
  *H04R 29/00*   (2006.01)
  *A61M 5/142*   (2006.01)
  *A61B 5/145*   (2006.01)
  *G10K 15/02*   (2006.01)

(52) U.S. Cl.
  CPC ........ *A61M 5/14244* (2013.01); *A61B 5/14532* (2013.01); *G10K 15/02* (2013.01); *H04R 29/00* (2013.01); *A61M 2205/186* (2013.01); *A61M 2205/581* (2013.01); *A61M 2205/70* (2013.01); *A61M 2205/702* (2013.01)

(58) Field of Classification Search
  None
  See application file for complete search history.

(56) References Cited

U.S. PATENT DOCUMENTS

| 4,275,388 A | 6/1981 | Hornung |
| 6,424,722 B1 * | 7/2002 | Hagen et al. .................. 381/314 |
| 2003/0114836 A1 * | 6/2003 | Estes et al. ................ 604/890.1 |
| 2008/0205678 A1 * | 8/2008 | Boguslavskij et al. ....... 381/312 |
| 2011/0221583 A1 * | 9/2011 | Yodfat et al. ............... 340/384.6 |

FOREIGN PATENT DOCUMENTS

| WO | 03/053498 A2 | 7/2003 |
| WO | 2008/077914 A2 | 7/2008 |
| WO | 2010/026580 A2 | 3/2010 |

* cited by examiner

*Primary Examiner* — Joseph Saunders, Jr.
*Assistant Examiner* — James Mooney
(74) *Attorney, Agent, or Firm* — Roche Diagnostics International AG

(57) ABSTRACT

An ambulatory medical device is presented. The ambulatory medical device comprises a function module to provide the intended functionality of the device, a controller module to control the device, a sound generation module with an acoustic transducer to produce an acoustic signal and a signal generator to drive the acoustic transducer with a certain frequency. The signal generation module is arranged within a housing of the device. A tuning module varies the frequency used by the signal generator to drive the acoustic transducer and determines one or more frequencies that correspond to an optimum sound level of the acoustic signal outside of the housing of the device. The optimum sound level of the acoustic signal is a maximum sound level outside of the housing of the device, and/or a maximum perceivable sound level as determined by a user.

15 Claims, 3 Drawing Sheets (a)

(b)

ACOUSTIC WARNING LEVEL OPTIMIZATION IN AMBULATORY MEDICAL SYSTEMS

CROSS-REFERENCE TO RELATED APPLICATIONS

This application is a continuation of PCT/EP2011/063809, filed Aug. 11, 2011, which is based on and claims priority to EP 10173658.5, filed Aug. 23, 2010, which is hereby incorporated by reference.

BACKGROUND

The present disclosure generally relates to ambulatory medical devices and, in particular, to ambulatory medical devices that provide acoustic warning signals, to methods to configure acoustic warning signal generation in such devices, and to devices for carrying out such a configuration.

Many medical devices are required to comply with strict requirements concerning providing warning signals to users and medical personnel that indicate potentially dangerous situations and incidents. Specifically, for medical devices that are intended to be carried by a user respectively patient during daily life, such as external ambulatory infusion devices and the like, regulatory requirements demand the provision of warning signals with a sound level over a minimum level, to ensure the audibility of the warning signal also in ambient noise situations.

External ambulatory infusion devices for the infusion of a liquid medicament over an extended time period are known in the art for a number of therapies. In particular, such devices form the basis for a state-of-the-art therapy of Diabetes Mellitus by CSII (Continuous Subcutaneous Insulin Infusion).

Insulin infusion devices are typically designed to be carried by a user continuously, night and day, and to be concealed from view. They are intended to infuse insulin to the patient substantially continuously according to a time-varying schedule and to infuse larger drug boluses on demand. Besides diabetes therapy, these devices may be used for a number of further therapies, such as cancer treatment or pain therapy, without requiring substantial modification. Other examples of ambulatory medical devices are diagnostic systems for the continuous monitoring of physiological parameters, such as glucose level monitoring devices.

Such devices have to be robust in design and need to be protected from various environmental influences such as humidity and dirt. Advantageously they are waterproof. These goals are achieved by providing the devices by hermetically sealed housings. As a result the fully assembled devices do not comprise openings. A small aperture, with a diameter of, for example, 1 mm, is typically provided for pressure equalization purposes, which is covered by a gas-permeable but liquid-proof membrane. Such apertures, however, do not significantly influence the sound transfer from inside of the device to the outside.

Ambulatory medical devices typically comprise an acoustical transducer, for generating audible alarm signals and/or for providing user feedback. Especially for acoustic warning signals, a high sound level is generally desirable, to ensure audibility also in noisy environments. Regulatory requirements often define a minimum sound level that has to be reached. Norm ISO 60601-1-8 for example requires an acoustic warning sound level of at least 50 dB.

Ambulatory medical devices are generally equipped with batteries. Furthermore, patients attach great importance to convenience and discretion. Thus, such devices should have small dimensions and a low weight. Because the sound can only be transmitted from the acoustical transducer, which has to be located within the sealed device, to the environment via the housing walls, a considerable attenuation occurs. Given the general design constraints for such devices, in particular with respect to size and power consumption, as well as the necessary hermetical sealing of the device housing, the provision of a sufficient acoustic warning sound level can be therefore a critical issue. For current devices it is known that alarms and acoustic warnings are sometimes not recognized if the medical device is in a pocket or the like, and there is a considerable ambient noise level.

Although modern production facilities allow the manufacture of medical devices and the basic components with high and constant quality, there will always be—within the defined tolerances—a remaining statistical spread of the characteristics of the single components as well as of the assembled device. Therefore certain operational parameters, such as for example the operational frequency of the acoustical transducer, have to be defined for an average case.

Therefore, there is a need for medical devices, such as, ambulatory medical devices that generate and configure acoustic warning signals with optimum sound volume. An optimum sound volume can be an optimum sound level achievable with a certain device and/or an optimum sound level perceivable by a certain user.

SUMMARY

According to the present disclosure, a device and method for configuring a sound generation module of an ambulatory medical device is presented. A test frequency can be determined. An acoustic signal can be generated with the sound generation module by applying the test frequency. A feedback signal can be obtained. The feedback signal can be processed to a feedback value. The feedback signal and value can be related to the sound level of the acoustic signal outside of a housing of the device. The determining, generating, obtaining and processing can be repeated for at least once for another test frequency. Based on the test frequencies and their corresponding feedback values, at least one optimum frequency can be determined that corresponds to an optimum sound level of the acoustic signal. The optimum sound level of the acoustic signal can be a maximum sound level outside of the housing of the device and/or a maximum perceivable sound level as determined by a user.

Accordingly, it is a feature of the embodiments of the present disclosure to provide medical devices, such as, ambulatory medical devices that generate and configure acoustic warning signals with optimum sound volume. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
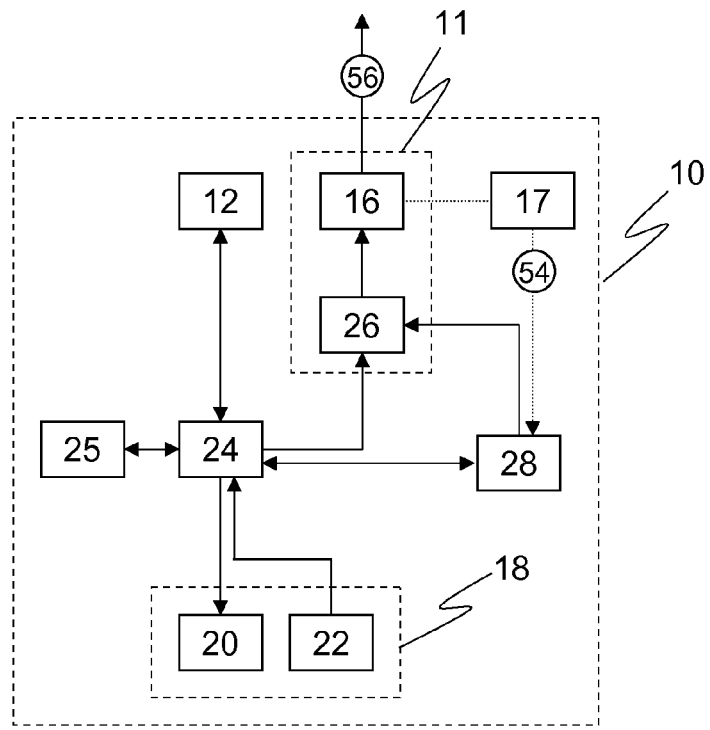
FIG. 1 illustrates schematically an ambulatory medical device with an internal tuning module according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The present disclosure aims to individually optimize the sound level of acoustic warning signals for each ambulatory medical device by tuning the frequency of the electrical signal that drives the acoustic transducer generating the warning signal to a value that can result in a maximum perceivable sound volume.

An ambulatory medical device can comprise a function module to provide the intended functionality of the device, a controller module to control the device, and a sound generation module with an acoustic transducer to produce an acoustic signal and a signal generator to drive the acoustic transducer with a certain frequency, wherein the signal generation module can be within a housing of the device. A tuning module can vary the frequency used by the signal generator to drive the acoustic transducer and determine one or more frequencies that correspond to an optimum sound level of the acoustic signal. The optimum sound level of the acoustic signal can be a maximum sound level outside of the housing of the device and/or a maximum perceivable sound level as determined by a user.

Within this disclosure, the term sound level or sound volume can include the physical sound amplitude, i.e. sound pressure, as well as the physiological sound amplitude, i.e. the perceived loudness.

Advantageously, the tuning module can comprise one or more sensors for obtaining feedback data directly and/or indirectly related to the sound level of the acoustic signal outside of the housing.

In one embodiment, the tuning module can measure an electrical, or mechanical, parameter of the acoustical transducer as a measure for the sound level generated by the transducer and can calculate the sound level outside of the housing of the device based on the sound level generated by the transducer and a given sound attenuation function of the housing. The electrical, or mechanical, parameter may for example be the electric current drawn by the transducer or the impedance of the transducer or the oscillation amplitude of a piezo crystal.

In another embodiment, the tuning module can measure an electrical, or mechanical, parameter of the acoustical transducer as a measure for the sound level generated by the transducer and can calculate the perceivable sound level outside of the housing of the device based on the sound level generated by the transducer and a given function providing the relation between perceived loudness and physical sound pressure. These latter two variants may also be combined.

In a further embodiment, the tuning module can comprise a microphone to measure a sound level outside of the housing of the device, an acceleration sensor to measure an acceleration of a portion of the housing walls, a vibration sensor to measure a vibration of a portion of the housing walls, and/or an optical distance measurement sensor to measure a deflection of a portion of the housing walls.

In the ambulatory device, the tuning module can be arranged fully or partially outside of the housing of the ambulatory medical device. In addition or alternatively, the tuning module can be arranged fully or partially in a physically separate unit of the ambulatory medical device. In one embodiment, such devices can comprise an interface to establish a data link between different parts of the tuning module.

An ambulatory medical device can be an infusion pump device, such as, for example, an insulin infusion pump device, or a device for monitoring the glucose level in the blood of a patient or any other ambulatory medical device where an acoustical warning signal needs to be provided.

In a method for configuring a sound generation module of an ambulatory medical device, a test frequency can be determined; an acoustic signal can be generated with the sound generation module, applying the test frequency; and a feedback signal can be obtained and processed to a feedback value. The feedback signal and value can be related to the sound level of the acoustic signal outside of a housing of the device. These steps can be repeated at least once for another test frequency. Based on the test frequencies and their corresponding feedback values, at least one optimum frequency can be determined that corresponds to an optimum sound level of the acoustic signal. The optimum sound level of the acoustic signal can be a maximum sound level outside of the housing of the device and/or a maximum perceivable sound level as determined by a user.

In one embodiment, the feedback signal can be an electrical, or mechanical, parameter of the acoustical transducer as a measure for the sound level generated by the transducer. The feedback signal can be processed to a feedback value can include calculating the sound level outside of the housing of the device as the feedback value based on the feedback signal and a given sound attenuation function of the housing.

In another embodiment, the feedback signal can be an electrical, or mechanical, parameter of the acoustical transducer as a measure for the sound level generated by the transducer. The feedback signal can be processed to a feedback value can include calculating the perceivable sound level outside of the housing of the device based on the sound level generated by the transducer and a given function providing the relation between perceived loudness and physical sound pressure. These latter two variants may also be combined.

In a further embodiment, the test frequency can be swept through a certain range. The feedback values can be stored as a function of the test frequency. The at least one optimum frequency can be determined by identifying extremes in the feedback value function.

A configuration module for configuring a sound generation module of an ambulatory medical device can comprise a sensor for measuring a feedback signal corresponding to the sound level generated by a sound generation module of the device, a signal processing module for processing the feedback signal to a feedback value, and an interface for communicating with the ambulatory medical device.

In one embodiment, the configuration module can comprise a controller module to control the frequency applied for the sound generation module of the device via the interface. Alternatively or in addition, the configuration module can temporarily store feedback values and determine extreme values in the stored feedback values. In one embodiment of such a configuration module, the module can store an attenuation curve comprising the attenuation by the housing of sound energy generated by an acoustical transducer inside the housing.

Referring initially to FIG. 1, an ambulatory medical device 10 with an internal tuning module 28 is schematically shown. The ambulatory medical device 10 can comprise a controller module 24, a function module 18, a sound generation module 11, and a user interface module 12.

In one embodiment, the function module 18 can be an infusion pump module of an infusion pump device. However, a similar setup can be applied for any ambulatory medical device with acoustic warning capabilities. The function module 18 of the infusion pump device 10 can comprise a drive system 20, one or more sensors 22, and other components that are not shown since they are not relevant for the acoustic warning capabilities.

The controller module 24 can typically be a microprocessor based controller. The controller module 24 can operate the function module 18 and can receive sensor data from the function module 18 to supervise the operation of the function module 18. The device 10 can further comprise a data interface (not shown) for connecting to a remote control device and/or a remote computer, and the like. Advantageously, such a data interface can be a wireless interface.

A memory module 25 can operationally be connected to the controller module 24 and can be foreseen to store configuration data and/or data related to the operation of the device 10.

The user interface module 12 can comprise one or more data inputs/outputs that can allow the user to receive information from the device 10 and to enter data or commands. The data inputs/outputs can comprise, for example, a screen for optically presenting data, a keypad or buttons to manually enter data, a touch screen, or the like.

Primarily, the sound generation module 11 can be intended to deliver acoustic warning signals to the user of the device 10. In the case of an infusion pump device, this warning can for example be related to a detected occlusion within the fluid system or another malfunction of the device 10 or an empty medicine reservoir. In addition, it can be used to provide the user with acoustical feedback. The sound generation module 11 can comprise an acoustical transducer 16 and a signal generator 26 providing an AC driving signal to the transducer 16. The signal generator 26 can be controlled by the controller module 24 and can generate a signal of sinusoidal, rectangular or any other wave form. A rectangular wave form can typically be applied due to its simple technical implementation. The signal generator 26 can generate signals of variable frequency.

For the acoustic transducer 16 various designs are known in the art. Typically, it can be a miniaturized dynamic loudspeaker or a piezo buzzer. A tactile indicator, such as a vibration-generating device, can also be understood to be an acoustic transducer 16, if it is driven by an AC signal.

For optimizing the acoustic alarm signal, particularly maximizing the sound level perceivable by the user, a tuning module 28 can be provided. The tuning module 28, which can be controlled by the controller module 24, can find the optimum operational frequency for the signal generator 26, which can be correlated to a maximum objective sound level.

It should be noted that for the purpose of illustration and clarity the controller module 24, the memory module 25, the signal generator 26 and the tuning module 28 are shown as separate structural blocks. In one embodiment, however, the modules can be realized as fully or partly integral electronic circuits. Advantageously, they can be part of the overall electronic circuitry board of the device 10.

At a certain optimum frequency, that is individual for every particular ambulatory device, the sound level that is perceivable outside of the housing can assume a maximum value. Among other factors, the optimum frequency can depend on the optimum operational frequency of the transducer 16, as well as the frequency dependent attenuation characteristics of the sealed housing of the device 10. To find this optimum operational frequency and to maximize the acoustic warning sound level, the sound level can be measured as a function of the signal frequency.

Since in an ambulatory device 10 as shown in FIG. 1, a direct measurement of the sound volume outside of the housing can be prevented by the hermetical sealing, an alternative feedback signal inside of the device 10 can be used, which can be correlated to the outside sound level. Which feedback signal is suitable and appropriately correlates to the sound level can depend on the particular design of the ambulatory medical device 10, such as, for example, the type of the acoustical transducer 16 used. Advantageously, the feedback signal can reach a maximum or minimum value at the resonance frequency of the transducer 16.

Figure 2:
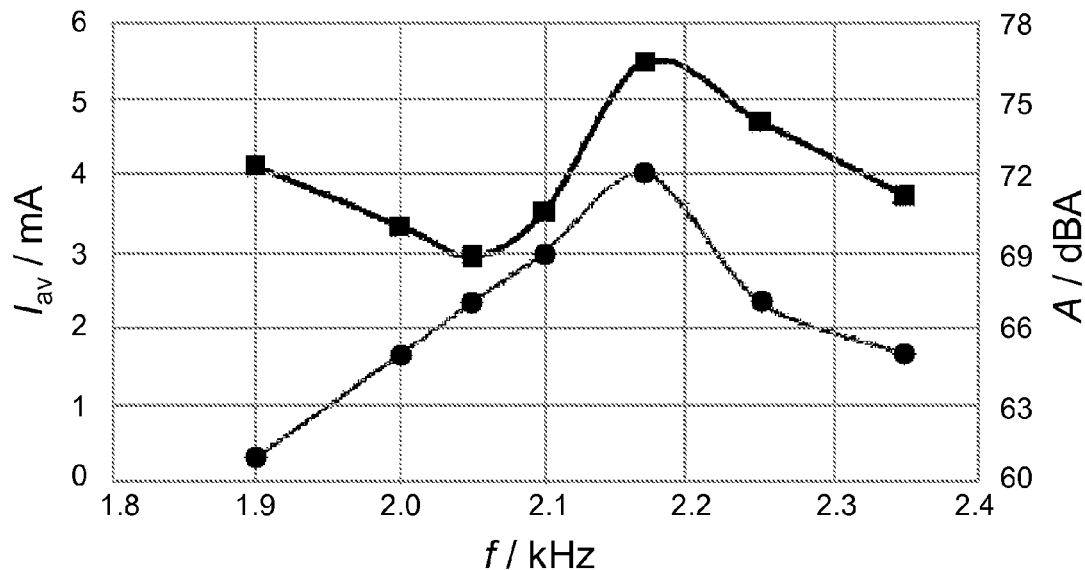
FIG. 2 illustrates (a) a graph displaying the current drawn by an acoustic transducer of an ambulatory medical device (squares), as a function of the signal frequency, as well as the resulting measured sound level (circles), and (b) an exemplary attenuation curve of a medical device housing (rectangles) and an exemplary sound amplitude level of the acoustic signal outside of the housing (triangles), calculated based on the attenuation curve and the determined sound level amplitude (circles) produced by an acoustic transducer inside the housing according to an embodiment of the present disclosure.
Figure 2:
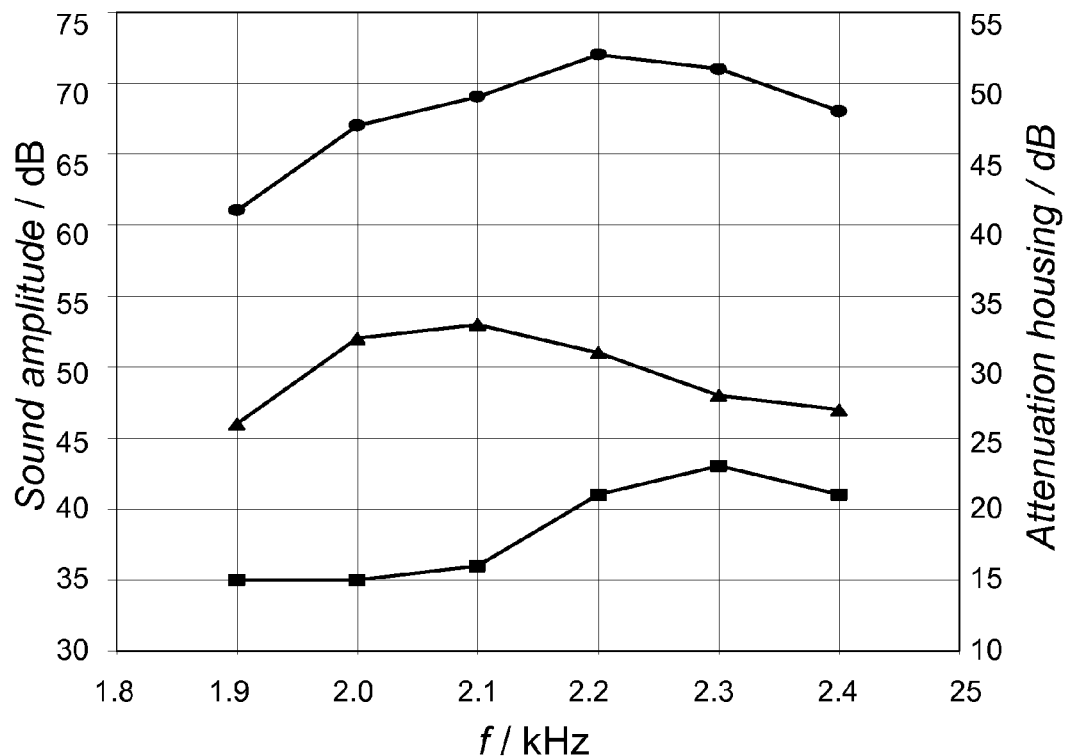

For example, the electric current drawn by a transducer 16 during operation, or its electrical resistance, can be utilized to find the optimum frequency for the transducer operation. FIG. 2(a) exemplarily shows the sound level (filled circles) of a miniaturized dynamic loudspeaker as the transducer 16, along with the current (filled squares) drawn by the loudspeaker, as a function of the applied drive frequency. The loudspeaker can be arranged in a closed housing, with the sound level being measured outside the housing. As can be seen, for this setup the drawn current can assume a maximum at the maximum sound level. Therefore, the sound level and the drawn current can correlate; the current can be a suitable feedback parameter.

However, depending on the construction of the housing, as well as the coupling of the acoustical transducer 16 to the housing, the attenuation of the housing may depend on the frequency. Depending on the resonant frequencies of the housing, the resulting perceivable sound amplitude outside the housing can be larger for a frequency off the optimum frequency of a transducer 16 than at the optimum frequency itself. The internal feedback parameter cannot take into account attenuation of the sound signal by the housing. To compensate this effect, in one embodiment an average attenuation curve of the housing can be applied to correct the optimum frequency in regard to the sound level outside of the housing.

In the device as shown in FIG. 1, the following procedure can be carried out to configure the sound generation module 11: The tuning module 28 can initiate a tuning process, by activating the sound generation module 11, such that an acoustical alarm signal 56 can be generated by the acoustic transducer 16, with a certain frequency delivered by the signal generator 26. The tuning module 28 can receive a feedback signal 54 from a sensor 17, wherein the feedback signal can be correlated to the sound level generated by the transducer 16.

The tuning module 28 can change the frequency used by the signal generator 26 to drive the transducer 16, according to a certain pattern. The tuning module 28 can for example increase the frequency stepwise or continuously, thereby sweeping through a defined frequency range. Alternatively, a limited set of frequencies within a defined range can be tested and the like.

During variation of the signal frequency, the tuning module 28 can compare the feedback signal 54 with the previously obtained feedback values, in order to find a maximum (or minimum, depending on the used feedback signal), that can be correlated to a maximum sound level of the acoustic transducer.

In case a housing attenuation curve is applied, theoretical sound amplitude outside of the housing can be calculated, based on the determined amplitude of the transducer 16 (feedback signal 54) and the assumed attenuation at the specific frequency value obtained from a stored attenuation curve. This calculated sound amplitude value can then be compared with the previously obtained calculated sound amplitude values. Once a maximum value is determined, the frequency variation can be stopped. The tuning module 28 can deliver the determined optimum drive frequency to the controller module 24, which can store the information in the configuration memory 25 to be used for alarm signal generation in the future. The configuration of the sound generation module 11 can be completed.

FIG. 2(b) exemplarily shows a calculated sound amplitude curve (triangles) perceivable outside of a housing. The amplitude can be calculated based on an average attenuation curve (rectangles) for a housing and a sound level amplitude inside the housing generated by the acoustical transducer 16 for a certain frequency, which can be determined directly or indirectly. While the optimum frequency for the acoustical transducer 16, corresponding to a maximum of sound energy generated by the acoustical transducer 16, can lie at approximately 2.2 kHz, the actually perceivable sound amplitude outside of the housing can have a maximum at about 2.1 kHz, since attenuation of the housing can decrease below about 2.2 kHz, for example, due to a resonance frequency in that range.

In a further embodiment, average human acoustic perception parameters can be taken into account, for example by providing a function that can allow to calculate a perceived loudness (for example, in phon units) from a physical sound pressure level (for example, in dB units).

The configuration procedure can be initiated in a number of ways. For example, the tuning process can be carried out in the production facility as part the general testing and configuration procedures following the device manufacture. Alternatively or additionally, the device user or a maintenance person may initiate the configuration procedure at his discretion. Alternatively or additionally, the configuration procedure can be initiated automatically on suitable occasions, for example each time a device battery is replaced, or a drug cartridge or another disposable component is changed. Such a repetition of the tuning process after production can allow compensating aging effects and the like.

Since an internal tuning module 28 can be realized with limited additional hardware and firmware effort, it can be implemented in the ambulatory medical device 10 at reasonable costs. An internal tuning module 28 can allow carrying out the optimization whenever required, as described above.

Figure 3:
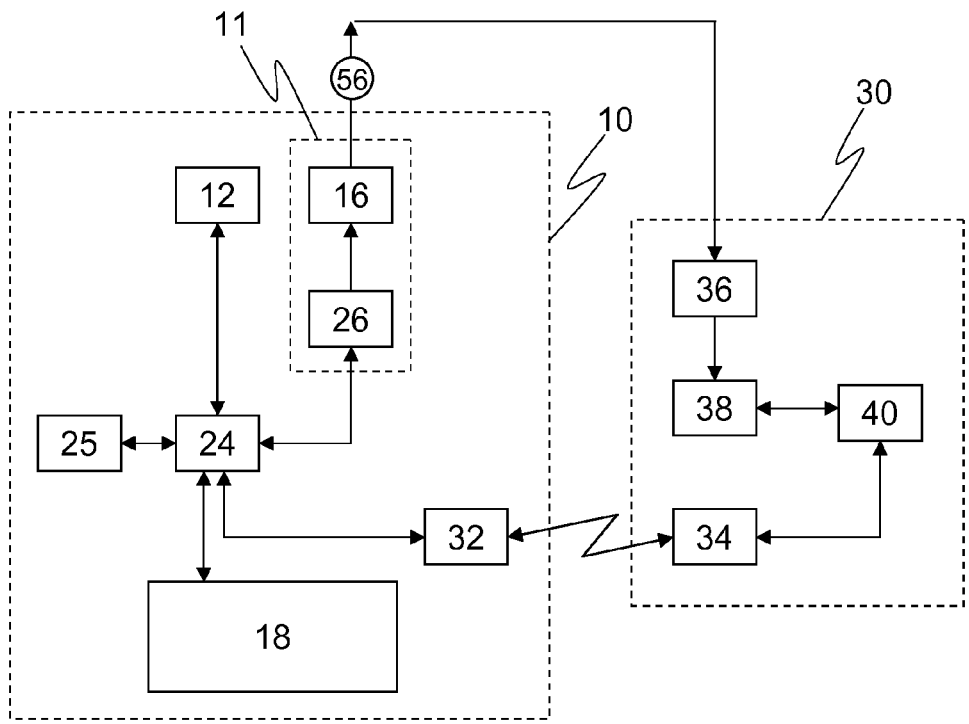
FIG. 3 illustrates schematically another ambulatory medical device operationally connected to an external tuning module according to an embodiment of the present disclosure.

FIG. 3 shows an embodiment of an ambulatory medical device 10 according to the invention that can be especially advantageous for use in the context of device configuration and setup at a production facility.

An external tuning module 30 can be provided that can temporarily operationally be connected to the ambulatory medical device 10, in order to tune the signal frequency to an optimum with maximum perceivable sound level. For that purpose, the ambulatory medical device 10 can be provided with a second interface 32, which can communicate with a corresponding interface 34 of the external tuning module 30. The second interface 32 may be particularly dedicated to this purpose or it can be identical with an interface 12 of the device 10 to communicate with a remote control device. The latter variant can have the advantage that no additional electronic components can be required.

Furthermore, the external tuning module 30 can comprise a sensor module 36 that can directly or indirectly measure the sound energy generated by the acoustic transducer 16 that can actually arrive outside. A signal processing module 38 can process the data received by the sensor module 36 to sound level data and a controller module 40 can assess the determined sound level data.

Via the interface 32, 34, the controller module 40 of the external tuning module 30 can instruct the sound generation module 11 of the ambulatory medical device 10 to activate and deactivate the acoustic transducer 16 and to change the operational frequency of the signal generator 26.

The sensor module 36 can for example be realized as a microphone, advantageously located in a defined position in regard to the device 10, to directly measure the sound level outside of the housing. The sound level can also be measured indirectly by determining the acceleration or the amplitude of deflection of certain parts of the housing walls, by an acceleration or vibration sensor that can be mechanically coupled to the housing of the device 10, or an optical distance measurement sensor that can measure the deflection of one or more defined portions of the housing.

The signal processor module 38 can typically include amplifiers, filters, analogue-to-digital conversion circuitry, and the like. The signal processor module 38 can further include non-linear circuitry, such as, for example, a logarithmic amplifier and an A-curve or C-curve filter, for simulating human hearing characteristics.

The interface 34, 32 between external tuning module 30 and ambulatory medical device 10 can be advantageously a wireless interface. It can be realized, for example, as an infrared interface or a short range radio frequency interface, for example, BlueTooth® (IEEE 802.15.1).

Via the data link established by interface 32, 34, the controller module 40 of the external tuning module 30 can instruct the controller module 24 of the ambulatory medical device 10 to change the frequency generated by signal generator 26. As previously described, a certain frequency range may be swept, while sampling the sound level data. In this case, the optimum frequency can advantageously be determined after completing the sweep through the frequency range. The resulting optimum frequency can then be communicated to the controller module 24 of the ambulatory medical device 10 and stored in the configuration memory 25 for later use. Alternatively, a stop signal may be transmitted to the ambulatory medical device 10 at the maximum sound level, thus stopping the sweeping.

The external tuning module 30 can either be realized as a stand-alone configuration device or as an integral part of a larger testing and/or configuration station, which can be used for testing further functions of the infusion device, writing configuration data into the device memory, or the like.

The advantage of the embodiment shown in FIG. 3 can be the measurement of the relevant parameter, namely the achievable sound level outside of the housing. Thus, not only the variability of individual resonance frequencies of the used acoustic transducer components can be taken into account, but also individual resonance frequencies of the housings, as well as the mechanical coupling between the transducer 16 and the housing, and the like.

As discussed above, the configuration procedure as such can be controlled and monitored by the external tuning module 30, sending instructions to the controller module 24 of the ambulatory device 10. Alternatively, however, the main control of the configuration procedure can be assigned to the ambulatory device 10 instead, namely to an internal tuning module 28. In this embodiment, the external tuning module 30 with the sensors can have the primary function of providing the internal tuning module 28 with the received sound level data either in raw form or already processed, while the optimum frequency can be determined internally. In another embodiment, the internal tuning module 28 can control the frequency variation, while the external tuning module 30 can return the determined optimum frequency to the internal tuning module 28.

Figure 4:
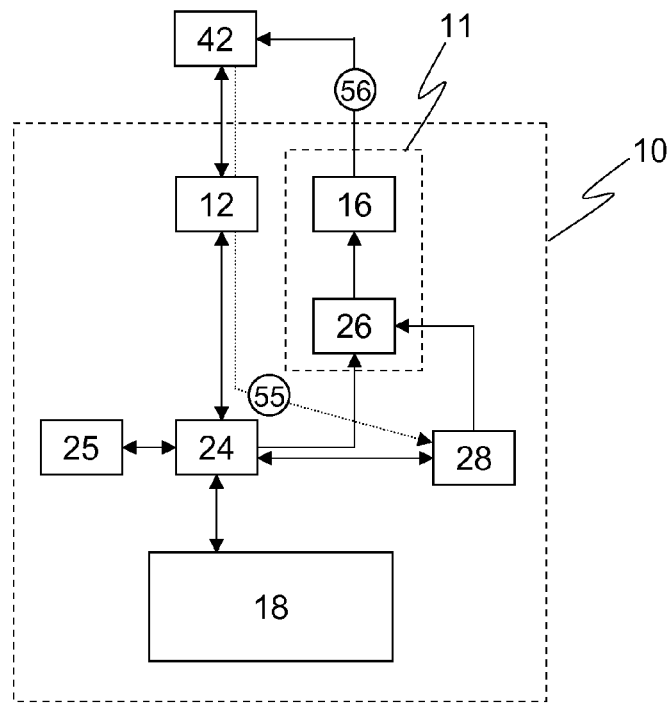
FIG. 4 illustrates schematically a further ambulatory medical device with a user providing feedback for the internal tuning module according to an embodiment of the present disclosure.

Yet another embodiment of an ambulatory medical device 10 is depicted in FIG. 4. In this embodiment, a device user 42 can assess the alarm sound level. After the user has initiated the configuration procedure, the tuning module 28 can vary the frequency used by signal generator 26, for example by sweeping through a certain frequency range. The user 42 can provide feedback of the perceived sound level via the user interface module 12 to the tuning module 28, which subsequently can determine an optimum frequency based on the user feedback. Thus, such an embodiment can allow optimizing the subjective sound level for a specific user, in contrast to the preceding embodiments, where the objective sound level, the measurable physical quantity, can be optimized.

Since it is not possible for humans to exactly quantify a perceived sound level, in one embodiment, the controller module 24 can present to the user a restricted number of acoustic signals with different frequencies. The user can then tag these alarm signals with a perceived qualitative sound level. For example, the user 42 can sort the acoustic signals in the order of increasing or decreasing sound volume. In the simplest case of only two signals with different frequencies, for example, the user can inform the tuning module 28 which signal he perceived to be louder. After collecting sufficient feedback data 54 from the user, the controller/tuning module 24, 28 can then determine the optimum frequency for the acoustic alarm signal.

In one embodiment, the controller module 24 can continuously adapt the frequencies presented to the user 42, based on the already obtained feedback data 54, in order to more efficiently determine the optimum frequency.

In a further embodiment, the signal generator 26 can slowly sweep through a frequency range, as long as the user 42 continues to press a defined button or the like of the user interface module 12, and can stop sweeping when the user 42 releases the button. The user 42 can press the button as long as the perceived sound level increases and can release the button when the perceived sound level decreases. This optimum frequency can then be stored in the memory 25 as the acoustic alarm frequency. The process may also be carried out in two steps, including a first coarse tuning, and a subsequent second fine tuning.

The advantage of the embodiment presented in FIG. 4 can be that the optimum frequency can be adapted to a specific, individual person, namely the user 42 carrying the ambulatory medical device 10. Thus, the determined frequency can take into account not only the relevant parameters related to sound generation and transmission, particularly the resonance frequencies of the acoustic transducer 16 and the device housing. In addition, the personal characteristics of the physiological sound perception of a specific person can be considered. The user 42 may have for example reduced or increased hearing capabilities in certain frequency ranges. Thus hardness of hearing, particularly in certain frequency ranges, or other user specific issues such as for example tinnitus can be automatically taken into account. Furthermore such a device 10 can require only minimal hardware and software effort.

Figure 5:
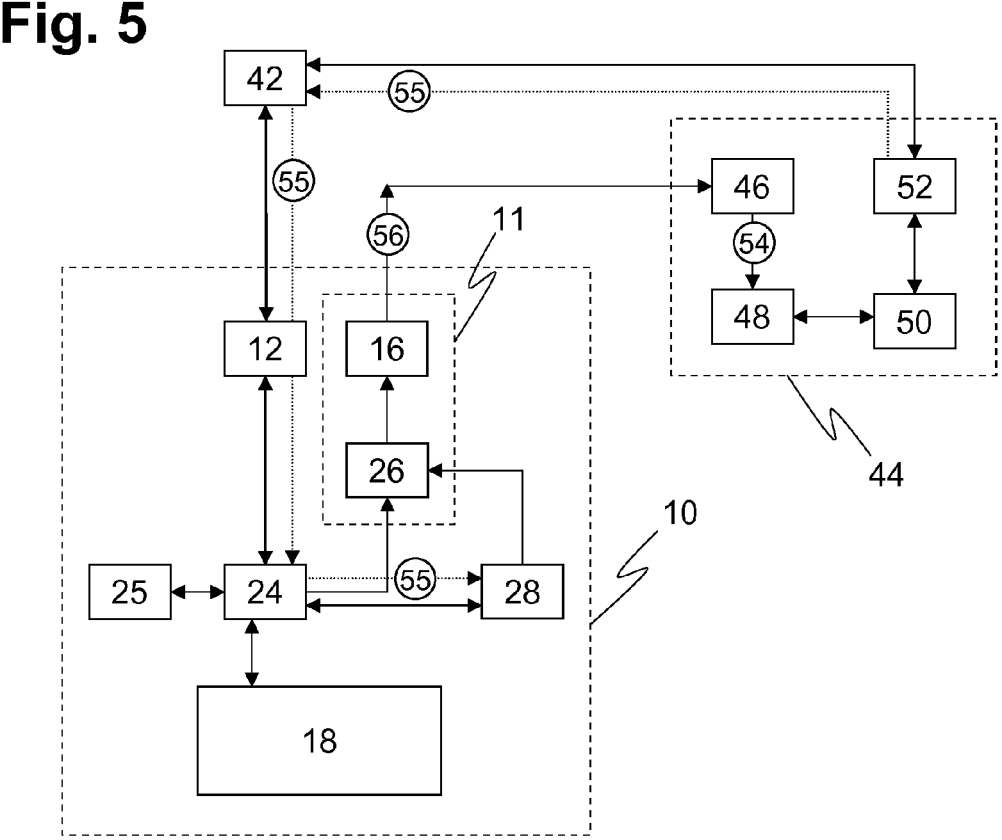
FIG. 5 illustrates schematically yet another ambulatory medical device with an external feedback module according to an embodiment of the present disclosure.

Yet another embodiment of an ambulatory medical device 10 is described in FIG. 5 with an external feedback module 44 measuring the sound level. After the user 42 has activated the external feedback module 44 and has initiated the tuning procedure via the interface 12, the internal tuning module 28 can change the frequency used by the signal generator 26 according to a defined pattern, for example, a sweep.

A sensor module 46 of the external feedback module 44 can receive the sound signal 56 produced by the acoustic transducer 16. A signal processing module 48 can determine the sound level and the controller module 50 can communicate the found sound level value in a suitable form to the user 42 via a user interface module 52, such as, for example, a screen. The user 42 can read the presented value and can enter the value into the ambulatory medical device 10 using the user interface module 12.

The particular advantage of this embodiment can be the fact that, on one hand, the sound level can be exactly quantified and that, on the other hand, no additional interface is necessary. The user 42 himself can transmit the feedback data 54 from the external feedback module 44 to the ambulatory medical device 10. Such an external feedback module 44 can be manufactured at comparably low costs, since as a minimum it has to comprise only a microphone, an on/off button, a few LEDs, and inexpensive integrated circuits. Such an embodiment can particularly be useful for example for first level support maintenance personnel or even the user 42 himself.

In one embodiment, an external tuning module 30 or an external feedback module 44 can be realized as an integrated part of a remote control module that can wirelessly communicate with the ambulatory medical device 10.

An advantageous device 10 can generate, during operation, signals of different frequencies, for example for distinguishing between alarms of primary importance that can require an immediate action, and further warnings or reminders of secondary importance. For such an embodiment, the above-defined procedure may be carried out separately for the different types of signals. The frequency range available for the different acoustic signal types can be sufficiently, such that the frequency ranges do not overlap and the signals can be clearly identifiable.

Besides the feedback that has been discussed so far, all suitable kinds of feedback can be applied whenever it can lead to a desirable optimization of the acoustic signal.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An ambulatory medical device, the ambulatory medical device comprising:
   a function module to provide the intended functionality of the device;
   a controller module to control the device;
   a sound generation module with an acoustic transducer to produce an acoustic signal;
   a signal generator to drive the acoustic transducer with a certain frequency, wherein the sound generation module is arranged within a housing of the device; and
   a tuning module that varies the frequency used by the signal generator to drive the acoustic transducer and determines one or more frequencies that correspond to an optimum sound level of the acoustic signal, wherein the optimum sound level of the acoustic signal is a maximum sound level outside of the housing of the device and/or a maximum perceivable sound level as determined by a user, wherein the tuning module measures an electrical, or mechanical, parameter of the acoustical transducer as a measure for the sound level generated by the transducer and calculates the sound level outside of the housing of the device based on the sound level generated by the transducer and a given sound attenuation function of the housing.

2. The device according to claim 1, wherein the tuning module comprises one or more sensors for obtaining feedback data directly and/or indirectly related to the sound level of the acoustic signal outside of the housing.

3. The device according to claim 1, wherein the tuning module comprises a microphone to measure a sound level outside of the housing of the device, an acceleration sensor to measure an acceleration of a portion of the housing walls, a vibration sensor to measure a vibration of a portion of the housing walls, and/or an optical distance measurement sensor to measure a deflection of a portion of the housing walls.

4. The device according to claim 1, wherein the tuning module is arranged fully or partially outside of the housing of the ambulatory medical device.

5. The device according to claim 1, wherein the tuning module is arranged fully or partially in a physically separate unit of the ambulatory medical device.

6. The device according to claim 5, wherein an interface establishes a data link between different parts of the tuning module.

7. The device according to claim 1, wherein the device is an infusion pump device.

8. The device according to claim 1, wherein the device is an insulin infusion pump device.

9. The device according to claim 1, wherein the device is a device for monitoring the glucose level in the blood of a patient.

10. A method for configuring a sound generation module of an ambulatory medical device, the method comprising:
    determining a test frequency;
    generating an acoustic signal with the sound generation module, applying the test frequency;
    obtaining a feedback signal;
    processing the feedback signal to a feedback value, wherein the feedback signal and value is related to the sound level of the acoustic signal outside of a housing of the device;
    repeating the determining, generating, obtaining and processing for at least once for another test frequency; and
    based on the test frequencies and their corresponding feedback values, determining at least one optimum frequency that corresponds to an optimum sound level of the acoustic signal, wherein the optimum sound level of the acoustic signal is a maximum sound level outside of the housing of the device and/or a maximum perceivable sound level as determined by a user, wherein processing the feedback signal to a feedback value includes calculating the sound level outside of the housing of the device as the feedback value based on the feedback signal and a given sound attenuation function of the housing.

11. The method according to claim 10, wherein the feedback signal is a parameter of the acoustical transducer as a measure for the sound level generated by the transducer.

12. The method according to claim 10, wherein the test frequency is swept through a certain range, the feedback values are stored as a function of the test frequency, and the at least one optimum frequency is determined by identifying extremes in the feedback value function.

13. A configuration module for configuring a sound generation module of an ambulatory medical device, the configuration module comprising:
    a sensor for measuring a feedback signal corresponding to the sound level generated by a sound generation module of the device;
    a signal processing module for processing the feedback signal to a feedback value; and
    an interface for communicating with the ambulatory medical device, wherein the configuration module stores an attenuation curve comprising the attenuation by the housing of sound energy generated by an acoustical transducer inside the housing.

14. The configuration module according to claim 13, further comprising,
    a controller module to control the frequency applied for the sound generation module of the ambulatory medical device via the interface.

15. The configuration module according to claim 13, wherein the configuration module temporarily stores feedback values and determines extreme values in the stored feedback values.

* * * * *